United States Patent

Duffy et al.

[11] 4,007,236
[45] Feb. 8, 1977

[54] BROMINATED PHOSPHORAMIDATES

[75] Inventors: James J. Duffy, Tonawanda; Richard D. Carlson, Grand Island, both of N.Y.; James C. Watson, Florence, S.C.

[73] Assignee: Hooker Chemicals & Plastics Corporation, Niagara Falls, N.Y.

[22] Filed: Dec. 31, 1974

[21] Appl. No.: 537,742

[52] U.S. Cl. .......................... 260/927 R; 260/937; 427/394; 428/276
[51] Int. Cl.[2] .......................................... C07F 9/15
[58] Field of Search ........................ 260/937, 927 R

[56] References Cited
UNITED STATES PATENTS

| | | | |
|---|---|---|---|
| 3,159,664 | 12/1964 | Bartlett | 260/937 |
| 3,597,503 | 8/1971 | Wilson et al. | 260/937 |
| 3,887,655 | 6/1975 | Shim | 260/937 |

FOREIGN PATENTS OR APPLICATIONS 2,146,988  5/1972  Germany ..................... 260/927 R

*Primary Examiner*—Anton H. Sutto
*Attorney, Agent, or Firm*—Peter F. Casella; Howard M. Ellis

[57] ABSTRACT

Brominated phosphoramidates of the structure

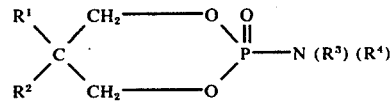

wherein $R^1$ and $R^2$ are independently selected from the group consisting of hydrogen, chloro, bromo, and chloro or bromo substituted alkyl of from 1 to 8 carbon atoms;

$R^3$ is selected from the group consisting of hydrogen, alkyl of from 1 to 8 carbon atoms, hydroxy substituted alkyl of from 1 to 8 carbon atoms and chloro or bromo substituted alkyl of from 1 to 8 carbon atoms;

$R^4$ is independently selected from the group consisting of $R^3$ and a group of the structure

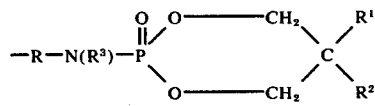

wherein R is selected from the group consisting of alkylene of from 2 to 8 carbon atoms; phenylene, biphenylene and dicyclohexylene; provided that at least one of $R^1$ and $R^2$ contains a bromine atom and at least one of $R^3$ and $R^4$ contains a replaceable hydrogen.

The phosphoramidates of the present invention are useful to impart a flame retardant property to combustible materials.

8 Claims, No Drawings

BROMINATED PHOSPHORAMIDATES

BACKGROUND OF THE INVENTION

Various materials have been suggested for imparting a flame retardant characteristic or property to combustible materials. Phosphorinanes are described in German Patent Application Nos. 2,146,988 and 2,327,185 as well as Swiss Patent Nos. 533,718 and 542,953. U.S. Pat. No. 3,456,041 teaches the use of phosphites and phosphonates of brominated pentaerythritol. U.S. Pat. No. 3,642,944 teaches fire retardant polyesters employing as a reactant dibromoneopentyl glycol. U.S. Pat. No. 3,324,205 teaches the use of halogenated phosphates and phosphonates as useful for flame retardant compositions. See also U.S. Pat. No. 2,828,288 for early disclosure of flame retardant compositions.

SUMMARY OF INVENTION

The invention is concerned with brominated phosphoramidates of the structure

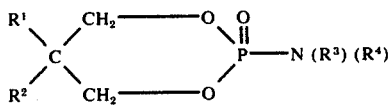

wherein:
$R^1$ and $R^2$ are independently selected from the group consisting of hydrogen, chloro, bromo, and chloro or bromo substituted alkyl of from 1 to 8 carbon atoms;

$R^3$ is selected from the group consisting of hydrogen, alkyl of from 1 to 8 carbon atoms, hydroxy substituted alkyl of from 1 to 8 carbon atoms and chloro or bromo substituted alkyl of from 1 to 8 carbon atoms;

$R^4$ is selected from the group consisting of $R^3$ and a group of the structure

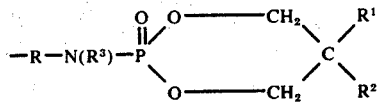

Wherein R is selected from the group consisting of alkylene of from 2 to 8 carbon atoms, phenylene, biphenylene and dicyclohexylene; provided that at least one of $R^1$ and $R^2$ contains a bromine atom and at least one of $R^3$ and $R^4$ contains a replaceable hydrogen.

The compounds of the present invention can be prepared in a number of ways. One method is the reaction of the appropriate halogenated glycol reactant with phosphoryl halide, such as a chloride ($POCl_3$) in a solvent such as tetrahydrofuran (THF) to produce the cyclic phosphoro halide. The cyclic material is then reacted with ammonia in a solvent such as tetrahydrofuran to produce the desired phosphoramidate. The N-methylol derivatives of the cyclic phosphoramidate are prepared by reacting it with formaldehyde or some equivalent trioxane.

It is to be appreciated that the di cyclic structure, the disphosphoramidate, can be prepared by reacting the cyclic phosphoro chloridate with an appropriate difunctional amine.

To produce the variations of compounds of the present invention the cyclic phosphoro chloridate may be reacted with the desired amine to give the appropriate $R_3$ and $R_4$ derivatives.

The compounds of the present invention may be used to impart flame retardant property or characteristic to combustible materials such as synthetic resins, wood, paper, cellulose containing fibers and fabrics, such as blends of cellulosic containing materials. In particular, the compounds of the present invention are useful for imparting flame retardant character to cellulosic containing fabrics.

DESCRIPTION OF PREFERRED EMBODIMENTS

As has been described above in the general preparation of the compounds of the present invention, the starting reactant is an appropriately selected halogenated glycol.

Suitable glycols are compounds as follows:

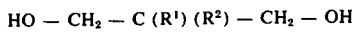

wherein $R^1$ and $R^2$ have the meaning defined above. Some preferred glycols are:

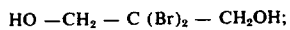

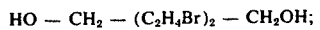

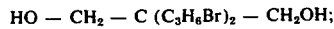

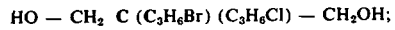

The most preferred glycol is dibromoneopentyl glycol. The basis for the selection of the preferred glycol is that a six-member cyclic compound is obtained in the first reaction between the glycol and the phosphoryl halide. This six membered ring has particular properties which are desirable in a composition which imparts flame retardancy to combustible materials. The six membered cyclic ring is highly stable. It has ultra violet and hydrolytic stability.

The compounds of the present invention are particularly useful for imparting flame retardant character to cellulosic materials such as cotton, rayon, paper, jute, ramie, wood and mistures thereof as well as blends of cellulosics, such as cotton or rayon with synthetic fibers, such as nylon, polyesters, acrylics and with proteinaceous fibers, such as wool and the like. The compounds of the present invention are particularly effective in imparting flame retardant character to cellulosic containing materials such as cotton and rayon, as well as blends of cellulosic materials such as polyesters, especially blends containing at least 50% weight of polyester, such as, 65%.

In applying the compounds of the present invention to cellulosic containing fabrics the usual process is to pad a solution of the compounds on to the fabric, dry the fabric and cure the composition. During the padding operation, the fabric is treated with a solution of the aforementioned chemical compositions. Frequently, before the flame retardant material is applied to the fabric, earlier pretreatments are undertaken such as desizing the fabric, washing and scouring in a commercially available detergent, bleaching of the fabric, washing the fabric again and then applying the compounds of the present invention. In some instances it is desirable that the fabric be dried prior to the application of the solution of the compounds of the present invention. It has also been found desirable to treat the fabric with a caustic washing (about 1 to 10% by weight alkali metal hydroxide, (such as sodium hydroxide) prior to the application of the compounds of the present invention.

While it is to be appreciated that the compounds of the present invention may be employed alone to impart flame retardant character to combustible materials, a preferred technique is to use the compounds of the present invention in conjunction with other phosphorus containing compositions which impart flame retardant character to combustible materials. The application of the compounds of the present invention with other phosphorus containing composition may be applied in a number of sequences. The first sequence and the most preferred sequence would be the application of a one bath composition containing the compounds of the present invention and the phosphorus containing compositions. Alternatively, the compounds of the present invention may be applied sequentially, that is, the fabric is treated with the compounds of the present invention and subsequently treated with a phosphorus containing composition. Alternatively, the sequential process can be reversed wherein the phosphorus containing materials are applied to the desired fabric and then the compounds of the present invention are applied onto the aforetreated fabric.

Numerous phosphorus containing compositions, which impart a flame retardant character to combustible composition are known in the art as well as their application. See for example U.S. Pat. No. 3,421,923 for description as to various techniques for applying phosphorous containing materials, which description is incorporated by reference.

Preferred phosphorous containing compositions that may impart flame retardant character to combustible materials are tetrakis (alpha-hydroxyorgano) phosphonium salts, such as the inorganic salts as the halides or sulfates and the like, or salts of organic materials as the acids, such as acetic, formic, oxalic and the like, or the product of neutralization of the tetrakis phosphonium compound with alkalic metal hydroxide or a tertiary amine. Another preferred phosphorous composition is Pyrovatex. [trademark of Ciba-Geigy, which has the chemical structure $(CH_3O)_2— P(O) — C_2H_4 — C(O)NHCH_2OH$].

The tetrakis (alpha-hydroxyorgano) phosphonium salt of the subject composition may be further defined as a compound having the formula:

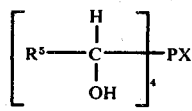

wherein $R^5$ is selected from the group consisting of hydrogen, lower alkyls having between about 1 and about 6 carbon atoms, halogenated lower alkyls having between about 1 and about 6 carbon atoms, lower alkenyls having between about 1 and about 6 carbon atoms, halogenated lower alkenyls having between about 1 and about 6 carbon atoms, aryls having between about 6 and about 10 carbon atoms, halogenated aryls having between about 6 and about 10 carbon atoms, cycloalkyls having between about 3 and about 6 carbon atoms, halogenated cycloalkyls having between about 3 and about 6 carbon atoms, and X is a halogen, such as chlorine, bromine, fluorine or iodine. Typical examples of suitable tetrakis (alpha-hydroxyorgano) phosphonium halide compounds are tetrakis (hydroxymethyl) phosphonium chloride, tetrakis (hydroxymethyl) phosphonium bromide, tetrakis (hydroxyethyl) phosphonium chloride, tetrakis (alpha-hydroxypropyl) phosphonium chloride, tetrakis (alpha-hydroxybenzyl) phosphonium chloride, tetrakis (alpha-hydroxymethyl cyclohexyl) phosphonium chloride, tetrakis (alpha-hydroxybutyl) phosphonium chloride and mistures thereof. The phosphonium compounds may be used in monomer form or in a partially polymerized form, so long as they are still water soluble. For example, tetrakis (hydroxymethyl) phosphonium chloride, which is the preferred phosphonium compound, may be heated to effect partial polymerization before dissolving it in the solution.

The tetrakis (alpha-hydroxyorgano) phosphonium hydroxide useful in the present invention may have the formula

wherein $R^5$ has the above described meaning. The preferred material is tetrakis (hydroxymethyl) phosphonium hydroxide.

In applying the composition of the present invention to a combustible substrate, the preferred technique is the application of a solution such as an aqueous solution. However, other solvents may also be employed providing the compounds of the present invention are soluble therein, such as dimethylformamide (DMF), THF, alkanols, of from 1 to 4 carbon atoms such as methanol, ethanol, butanol, aromatic solvents such as benzene, toluene, xylene or chlorinated hydrocarbons having from 1 to 4 carbon atoms such as carbon tetrachloride and the like.

The compounds of the present invention when applied to the fabric, should be applied such that there is a wet pick-up add-on of from 70 to 130% resulting in a resin add-on of from about 1 to 50% preferably about 5 to 35% and even more preferably of about 10 to about 25%. When the compounds of the present invention are used in one bath in conjunction with phosphorous compositions that impart flame retardant character, the ratio of the compounds on a weight basis should be from 1 – 10; 10 – 1 of brominated phosphoramidate; other phosphorous containing compositions.

The most preferred composition of the present invention is the N-methylol derivatives used in conjunction with tetrakis (hydroxymethyl) phosphonium chloride or hydroxide.

When a solution of tetrakis (hydroxymethyl) phosphonium hydroxide is used to impregnate the cellulose containing meterial there is an equilibrium between it and tris (hydroxymethyl) phosphine. Such a solution is well known in this art and can be prepared by reacting an aqueous solution of tetrakis (hydroxymethyl) phosphonium chloride with an approximately equimolar quantity of an organic or inorganic base, preferably sodium hydroxide. The pH of the final solution is adjusted to from 7 to 9 and preferably to from 7.5 to 8.1. For the purpose of this invention, the active component of the aqueous solution is considered to be tetrakis (hydroxymethyl) phosphonium hydroxide.

The aqueous treating solution may be applied to the cellulosic material in any convenient manner. For example, the solution may be applied by padding, dipping spraying, and the like. After impregnation, the excess solution is preferably removed from the material by passing the material through squeeze rolls, centrifuging, wringing, or other methods. Although a wet pick-up of from about 50 to about 200% may suitably be used, preferably the material contains about an equal weight, i.e., about 100% pick-up, of the treating solution.

Having described the invention in general, we can now turn to alternative embodiments of the invention. All percentages are percentages by weight and all temperatures are in degrees centigrade, unless otherwise indicated.

EXAMPLE 1

A 5-liter flask was charged with 306 g (2.0 mols) POCl₃ and 1400 ml/THF (tetra hydrofuran) and blanketed with nitrogen. To this was added dropwise 524 g (2.0 mols) of dibromoneopentyl glycol dissolved in 1000 ml THF. The mixture was heated to 50° during the addition and maintained there for 2.5 hours, keeping the mixture under nitrogen continuously. The mixture was stirred at room temperature for 48 hours.

Ammonia was bubbled through the mixture at 45°–55° for 4 hours. The mixture was then filtered, yielding 685g of precipitate with approximately 2000ml filtrate. The filtrate was stripped to final conditions of 5 mmHg and 70° C, yielding 412 g (64% of theory) of product, a yellowish gummy solid. The compound produced had the structure mixture was neutralized with dilute HCl, and this solvent was stripped off to final conditions of 70° and 20 mm Hg for 2 hours, yielding 156g (66% of theory) of residue product, a yellowish viscous substance having the structure

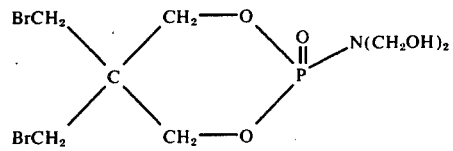

EXAMPLE 3

A 500 ml flask was charged with 100 g. (.292 mole) of dibromoneopentyl phosphorochloridate and 150 ml THF. The mixture was heated to 45°, and 17.5 g (.292 mole) of ethylene diamine was added dropwise. The temperature was maintained at 45°–55° with an ice bath. The mixture was then allowed to cool to room temperature, and filtered to remove the hydrochloride. The filtrate was then stripped to final conditions at 70° and 20 mmHg for 2 hours, yielding 73 g (75% of theory) of product. NMR Analysis confirmed the structure as:

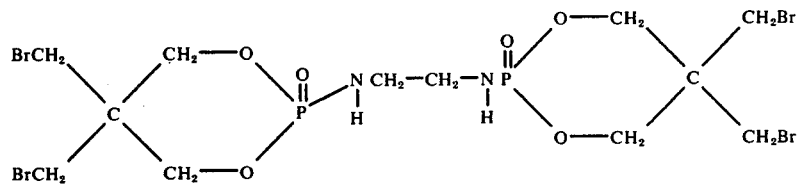

EXAMPLE 4

A 1-liter flask was charged with 100 g (.149 mole) of the product of Example No. 3 and 9 g (.298 mole) paraformaldehyde in 500 ml methanol. The pH was adjusted to 8-10 with sodium methoxide, and the mixture was refluxed for 4 hours. The mixture was neutralized with HCl, and allowed to stand for 48 hours. The solvent was stripped to final conditions of 0.5mm Hg and 70° for 1 hour, yielding 100g of residue product (92% of theory) and having the structure listed below.

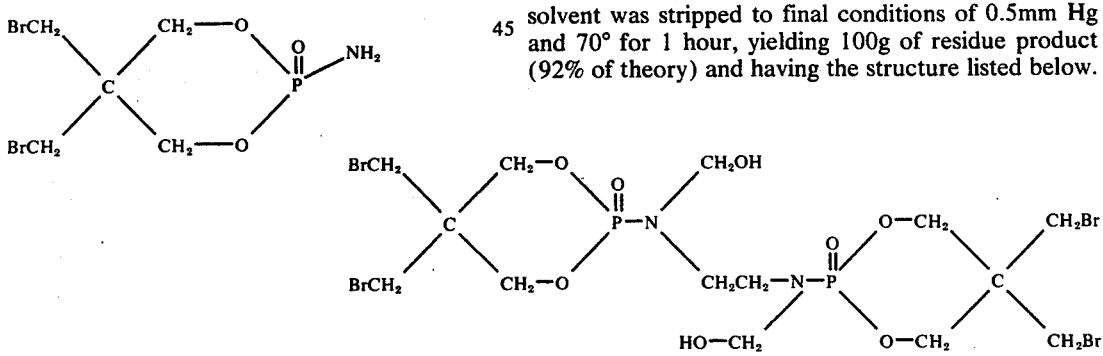

EXAMPLE 2

A 2-liter flask was charged with 200 g (.62 mole) of dibromoneopentyl phosphoramidate, 1000 ml of methanol and 37.2 g (1.24 moles) of trioxymethylene (trioxane). The pH was adjusted to 8- 10 with sodium methoxide, and the mixture was refluxed for 3 hours. The

EXAMPLE 5

A 500 ml flask was charged with 100 g (.292 moles) of dibromoneopentyl phosphorochloridate and 150 ml THF. Then 34.5 g (.584 mole) of n-propyl amine was added dropwise to the mixture, maintaining the temperature at 45°–55° with an ice bath. The solvent was then stripped to final conditions of 70° and 20 mm for 2 hours. The product was then washed with hot water, the water was decanted off, and benzene was added.

The mixture was then stripped to final conditions of 70° and 20 mm for 2 hours. The structure below was confirmed by NMR analysis.

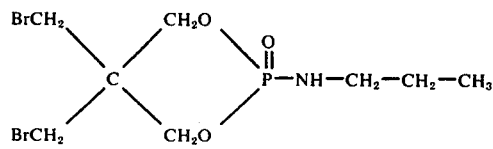

It is to be appreciated that a wide variety of primary amines may be used, in place of n-propyl amine, such as alkyl amines other than those containing propyl, such as methyl amine, ethyl amine, butyl amine, octyl amine and the like, alkanol amines as hydroxyl ethyl amine, hydroxy propyl amine, hydroxy butyl amine, hydroxy octyl amine, and the like.

EXAMPLE 6

A 250 ml flask was charged with 38 g (.104 mole) of the product of example No. 5 and 3.1 g (.104 mole) of paraformaldehyde in 100 ml of methanol. The pH was raised to 8-10 with sodium methoxide, and the mixture was refluxed for two hours. The mixture was then stripped to final conditions of 5mmHg and 70° for 1.5 hours, yielding a residue product of 25 g (61% of theory). The product is the N - methylol derivative of the product of Example 5 having the structure

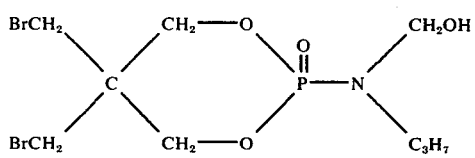

EXAMPLE 7

General Example for Application to Cloth

Samples of fabric were cut to approximately 15 in. × 24 in. size and immersed in a pad solution of the composition listed below. Samples were squeezed in a 2 roll laboratory padder with the pad pressure adjusted to give approximately 90 – 100% wet pick-up. Samples were then dried by being hung in a circulating air oven for the time temperature indicated in the following table. Samples were then cured at the time and temperatures indicated in the circulating air oven.

After cooling to room temperature, the samples were washed in a Sears washing machine with the following added to the wash water, sodium perborate (20 gr) soda ash (30 gr) Orvus detergent (30 gr)sold under the name Tide, which is a phosphate based detergent, for one cycle. The samples were then dried in a tumble dryer, being overnight in the laboratory and then weighed to determine initial resin add-on. Oxygen index was then determined.

To determine durability the samples were washed 10 cycles in a Sears home washer with 50 gr. of Orvus detergent added per wash cycle. At the end of 10 washings, the samples were dried in a tumble dryer and hung overnight prior to testing. Oxygen indices of the initial fabric were as follows:

| | |
|---|---|
| Cotton | 19 |
| 50/50 Polyester/Cotton | 19 |
| 65/35 Polyester/Cotton | 19 |

A solution was formulated of the following components and applied to cloth samples as described above.

| Formulation | Parts by Weight |
|---|---|
| Product of Example 4 | 25 |
| Tetrakis (hydroxymethyl) phosphonium chloride (30% by Wt) | 20 |
| Triethanol Amine | 20 |
| NaOH(50%) | 3 |
| $H_2O$ | 32 |

The flame retardant character was determined as shown in Table No. 1.

TABLE I

| Sample | A | B | C |
|---|---|---|---|
| Fabric (cotton or polyester/cotton blend | Ctn | 50/50 | 65/35 |
| Percent Wet Pick-up | 93 | 96 | 93 |
| Drying Time (min.) | 2.5 | 2.5 | 2.5 |
| Drying Temperature (° F) | 200 | 200 | 200 |
| Cure Time (min.) | 3.5 | 3.5 | 3.5 |
| Cure Temperature (° F) | 300 | 300 | 300 |
| % Resin Add-on | 14.2 | 16.3 | 20.0 |
| Initial Oxygen Index | 29 | 26 | 25 |
| Oxygen Index After 10 Home Washings | 27 | 25 | 24 |

EXAMPLE 8

Following the same procedure of Example 7, the following composition was formulated.

| Formulation | |
|---|---|
| Product of Example 4 | 40 Parts |
| Trimethylol Melamine | 30 Parts |
| Water | 27.5 Parts |
| $Zn(NO_3)_6 2H_2O$ | 2.5 Parts |

The resulting flame retardant tests are shown in Table II.

TABLE II

| Sample | A | B | C |
|---|---|---|---|
| Fabric (cotton or polyester cotton | Cotton | 50/50 | 65/35 |
| Percent Wet Pick-up | 100 | 105 | 95 |
| Drying Time (min.) | 2.5 | 2.5 | 2.5 |
| Drying Temperature (° F) | 200 | 200 | 200 |
| Cure time (min.) | 3.5 | 3.5 | 3.5 |
| Cure Temperature (° F) | 300 | 300 | 300 |
| % Resin Add-on | 11.7 | 16.6 | 12.0 |
| Initial Oxygen Index | 23 | 24 | 23 |
| Oxygen Index After 10 Home Washings | 24 | 23 | 23 |

EXAMPLE 9

A 50% mixture of N-methylol dibromoneopentyl phosphoramidate and subsequent dilutions was padded on cotton cloth at a pad pressure of 60 pounds per in² and treated as indicated in Table III.

TABLE III

| Sample | A | B | C | D |
|---|---|---|---|---|
| Padding | 50% | 40% | 30% | 20% |
| % Wet Pick-up | 115 | 98 | 94 | 90 |
| Drying Time | 5 min. | 5 min. | 5 min. | 5 min. |
| Drying Temp. | 200° F | 200° F | 200° F | 200° F |
| % Resin | 34 | 26 | 21 | 14 |
| OI | 38 | 34 | 32 | 29 |

EXAMPLE 10

A 50% mixture of N-methylol dibromoneopentyl phosphoramidate and subsequent dilutions was padded on 50/50 polyester/cotton cloth at a pad pressure of 30 pounds per in² and treated as indicated in Table IV.

TABLE IV

| Sample | A | B | C | D |
|---|---|---|---|---|
| Padding | 50% | 40% | 30% | 20% |
| % Wet Pick-up | 111 | 104 | 101 | 97 |
| Drying Time | 5 min. | 5 min. | 5 min. | 5 min. |
| Drying Temp. | 200° F | 200° F | 200° F | 200° F |
| % Resin | 35.5 | 28 | 22 | 15 |
| OI | 36 | 34 | 32 | 30 |

EXAMPLE 11

A 50% mixture of N-Methylol dibromoneopentyl phosphoramidate and subsequent dilutions was padded on 65/35 polyester/cotton cloth at a pad pressure of 30 pounds per in² and treated as indicated in Table V.

TABLE V

| Sample | A | B | C | D |
|---|---|---|---|---|
| Padding | 50% | 40% | 30% | 20% |
| % Wet Pick-up | 105 | 100 | 97 | 94 |
| Drying Time | 5 min. | 5 min. | 5 min. | 5 min. |
| Drying Temp. | 200° F | 200° F | 200° F | 200° F |
| % Resin | 34.5 | 29 | 22 | 16.5 |
| OI | 35 | 34 | 31 | 29 |

EXAMPLE 12

A composition containing 85 parts of the compound of Example 5, 50 parts trimethylol melamine (50% in H₂O), 5 parts ZN(NO₃)₂ · 6H₂O and 60 parts DMF was padded onto fabric samples (according to the procedure of Example 7) with the results of flame retardancy testing shown in Table VI.

TABLE VI

| Sample | A | B | C |
|---|---|---|---|
| Fabric (cotton or polyester/cotton) | 65/35 | 50/50 | Cotton |
| Percent Wet Pick-up | 98 | 107 | 113 |
| Drying Time (min.) | 2.5 | 2.5 | 2.5 |
| Drying Temperature (° F) | 200 | 200 | 200 |
| Cure Time (min.) | 4.0 | 4.0 | 4.0 |
| Cure Temperature (° F) | 330 | 330 | 330 |
| % Resin Add-on | 32 | 34 | 34 |
| Initial Oxygen Index | 33 | 34 | 39 |
| Oxygen Index After 10 Home Washings | 30 | 25 | 29 |

EXAMPLE 13

To the 30% solution remaining from the formulation in Example 12 was added 50 gr of tetrakis (hydroxymethyl) phosphonium chloride (80%). This solution was padded on the fabric at a pad pressure of 30 pounds per in² treated as shown in Table VII.

TABLE VII

| Sample | A | B |
|---|---|---|
| Fabric (polyester/cotton) | 65/35 | 50/50 |
| Percent Wet Pick-up | 92 | 105 |
| Drying Time (min.) | 2.5 | 2.5 |
| Drying Temp. (° F) | 200 | 200 |
| Cure Time (min.) | 4.0 | 4.0 |
| Cure Temp. (° F) | 330 | 330 |
| % Resin Add-on | 16.7 | 16.8 |
| Initial Oxygen Index | 28 | 29 |
| Oxygen Index After 10 Home Washings | 29 | 26 |

EXAMPLE 14

The following formulation was prepared and applied to fabric according to the procedure to Example 7 with the results of flame retardancy testing shown in Table VIII.

| Formulation | Parts by Weight |
|---|---|
| Product of Example 2 | 120 |
| Zn(NO₃)₂6H₂O | 8 |
| DMF | 190 |
| Trimethylol Melamine (50%) | 150 |

TABLE VIII

| Sample | A | B | C |
|---|---|---|---|
| Fabric (cotton or polyester/cotton) | 65/36 | 50/50 | Cotton |
| Percent Wet Pick-up | 96 | 96 | 102 |
| Drying Time (min.) | 2.5 | 2.5 | 2.5 |
| Drying Temperature (° F) | 200 | 200 | 200 |
| Cure Time (min.) | 3.5 | 3.5 | 3.5 |
| Cure Temperature (° F) | 330 | 330 | 330 |
| % Resin Add-on | 11.8 | 9.0 | 13.0 |
| Initial Oxygen Index | 22 | 22 | 25 |
| Oxygen Index After 10 Home Washings | 22 | 21 | 22 |

We claim:
1. Brominated phosphoramidates of the structure

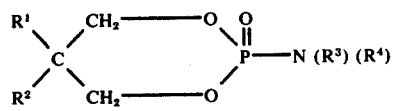

wherein:
R¹ and R² are independently selected from the group consisting of hydrogen, chloro, bromo and chloro or bromo substituted alkyl of from 1 to 8 carbon atoms;
R³ is selected from the group consisting of hydrogen, alkyl of from 1 to 8 carbon atoms, hydroxy substituted alkyl of from 1 to 8 carbon atoms and chloro or bromo substituted alkyl of from 1 to 8 carbon atoms;
R⁴ is a group of the structure

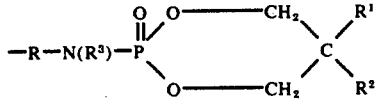

wherein R is selected from the group consisting of alkylene of from 2 to 8 carbon atoms, phenylene, biphenylene and dicycloheylene provided that at least one of $R^1$ and $R^2$ contains a bromine atom and at least one of $R^3$ and $R^4$ contains a replaceable hydrogen.

2. The compound of claim 1 wherein $R^1$ is a bromo substituted alkyl.

3. The compound of claim 2 wherein $R^2$ is a bromo substituted alkyl.

4. The compound of claim 1 wherein $R^3$ is a hydroxy substituted alkyl.

5. The compound of claim 5 wherein R is an alkylene group.

6. The compound of claim 1 of the formula

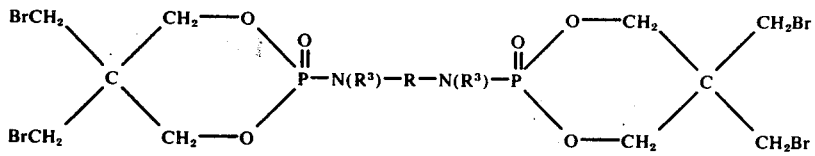

7. The compound of claim 1 of the formula

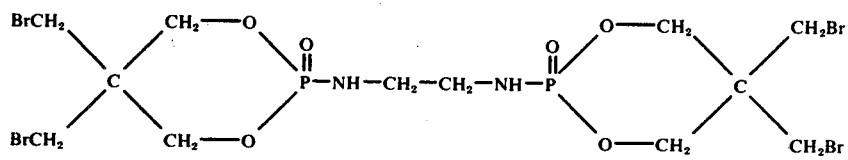

8. The compound of claim 1 of the formula

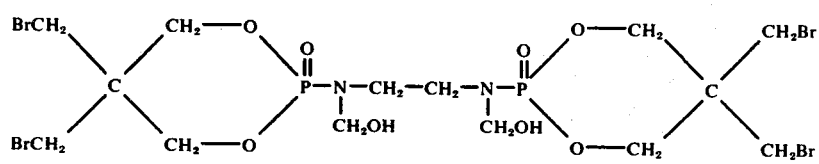

* * * * *